(12) United States Patent
Li et al.

(10) Patent No.: US 7,931,691 B2
(45) Date of Patent: Apr. 26, 2011

(54) EXTERNAL PROXIMAL FEMORAL PROSTHESIS FOR TOTAL HIP ARTHROPLASTY

(76) Inventors: Xue Li, Ashland, MA (US); Ping Xie, Ashland, MA (US); Kerry Y Xie, Baltimore, MD (US)

( * ) Notice: Subject to any disclaimer, the term of this patent is extended or adjusted under 35 U.S.C. 154(b) by 458 days.

(21) Appl. No.: 11/426,995

(22) Filed: Jun. 28, 2006

(65) Prior Publication Data

US 2008/0004711 A1    Jan. 3, 2008

(51) Int. Cl.
*A61F 2/36* (2006.01)

(52) U.S. Cl. .................. 623/23.12; 623/22.43; 623/22.4

(58) Field of Classification Search ............... 623/22.41, 623/22.43, 22.44, 22.46, 23.12, 23.14, 23.21, 623/23.22, 23.26–23.28, 22.4
See application file for complete search history.

(56) References Cited

U.S. PATENT DOCUMENTS

| | | | |
|---|---|---|---|
| 4,550,448 A | 11/1985 | Kenna | |
| 4,846,841 A | 7/1989 | Indong | |
| 4,976,740 A | 12/1990 | Kleiner | |
| 5,004,476 A | 4/1991 | Cook | |
| 5,007,935 A | 4/1991 | Vincent | |
| 5,133,769 A | 7/1992 | Wagner | |
| 5,376,126 A * | 12/1994 | Lin | 623/23.11 |
| 5,571,203 A * | 11/1996 | Masini | 623/22.46 |
| 5,725,593 A | 3/1998 | Caracciolo | |
| 6,383,227 B1 | 5/2002 | Baroud | |
| 6,488,716 B1 | 12/2002 | Huang | |
| 6,706,073 B2 * | 3/2004 | Draenert et al. | 623/22.46 |
| 7,255,717 B2 * | 8/2007 | Park et al. | 623/23.12 |
| 2003/0195635 A1 * | 10/2003 | Crofford | 623/22.46 |
| 2004/0260399 A1 * | 12/2004 | Chieng | 623/22.12 |

FOREIGN PATENT DOCUMENTS

| | | |
|---|---|---|
| CN | 98200233 | 1/1998 |
| CN | 02238101.5 | 8/2003 |
| WO | WO 2004043277 A1 * | 5/2004 |

OTHER PUBLICATIONS

Gerald A.M. Finerman etc. Total Hip Arthroplasty Outcomes. 1998.
Lars Carlson Femoral Neck Retention in Hip Arthroplasty; Acta Orthop Scand (1998) 59 (1) 6-8.
O. S. Imura Hip Mechanics; 1993.
M. A. Freeman. Why Reset the Neck? J. Bone Joint Surg. (1986) 68-B 346-349.
Paul G.J. Maquet Biomechanics of the hip. 1985.

* cited by examiner

*Primary Examiner* — Bruce E Snow
*Assistant Examiner* — Melissa Hoban

(57) ABSTRACT

A external femoral component for mechanically housing onto exterior remnant of natural femur and coupling with articulation elements in order to use in total hip arthroplasty defines as a hollow shell comprised of asymmetrically bell shaped cup, at least one rigid elongated stem downwardly extended from the lower rim of the cup and a plurality of an cylindrical object upwardly protruded from top of the cup for pairing with articulation elements and coupling with anchoring means and the tension anchoring means fixes the hollow shell on the bone surface through an interlocking mechanisms.

8 Claims, 7 Drawing Sheets

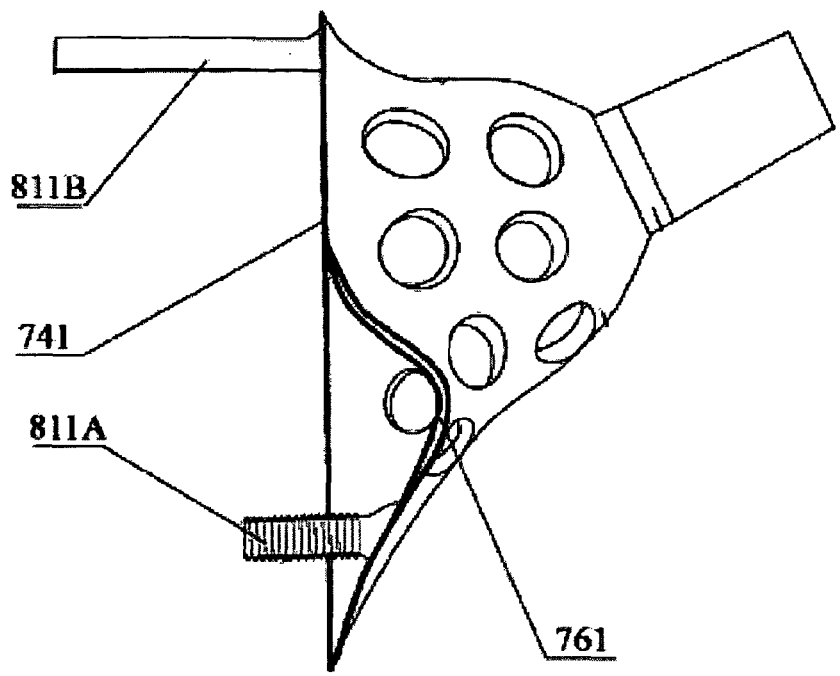
Fig. 3b
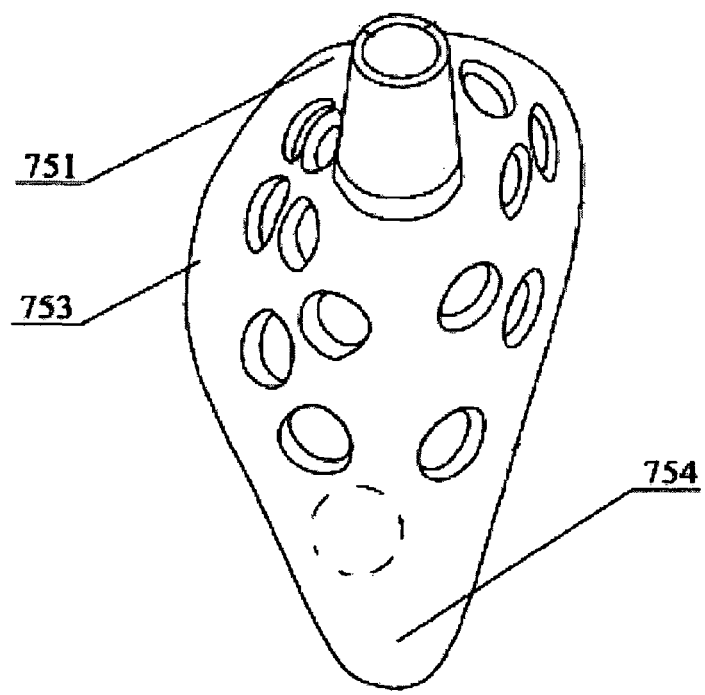

EXTERNAL PROXIMAL FEMORAL PROSTHESIS FOR TOTAL HIP ARTHROPLASTY

FIELD OF THE INVENTION

The present invention relates to a femoral prosthesis to be applied in total hip arthroplasty (THA). More specifically, the prosthesis is an external proximal femoral component and is housed on the outer area of remnant of proximal femur, which includes inferior retention neck, the trochanteric bed and inferior medial ridge of the proximal femoral shaft, and is mechanically fastened by a tension anchoring means during the installation.

DESCRIPTION OF THE PRIOR ART

In a natural human femur, most of loading force of the hip is placed on the head first and downwardly distributed through the hard cortex of the femoral neck and further conducted to the femur shaft, eventually to the knee joint. The quality of bone and its peripherals are key factors in the functionality of the hip joint. As well known, proper loading stress and its orientation on the bone can stimulate and facilitate bone growth and regeneration, in terms of its quality (density) and orientation of growth. There is a range of optimal stress which should be placed on the bone. For instance, if too little stress is applied to the bone, resorption can occur, leading to atrophy of the affected area. By same token, if too much stress is applied, it may also lead to resorption, or may result in an undesirable atrophy of the affected area. In addition, blood circulation and nutrient supply to the bone are also key factors in keeping the joint and bone in good condition (quality and functioning). However, any failure or defect of the factors above leads to bone disease or joint malfunction.

If the femoral head becomes diseased or damaged, it can be replaced with a prosthetic femoral component, such as total hip arthroplasty (THA). A popular THA procedure uses a stem hip prosthesis. THA has been a tremendously successful surgical invention for patients with disabling arthritis of the hip. The quality of life is predictably improved following THA.

The conventional stem design has been used in clinical THA practice for a few decades and its disadvantages have been identified. 1) The bending moment that is applied through an inter-modularly stem results in stress concentrations at points of the proximal, medial and the distal lateral ends of the prosthesis, respectively, which has been considered as a relatively small area for loading large force in comparison with area of natural femoral head. 2) The axial loads and torsional moments are transferred to the bone across the bone-prosthesis interface resulting in high shear stresses at the interface. 3) Due to the high stiffness of the prosthesis, there is a reduction in bending displacements, resulting in stress shielding in most of the area between bone and prosthesis. This disparity in stiffness also contributes to interface shear stresses. 4) There is also poor blood circulation around implanted prosthesis, causing the bone quality to decrease with time. As a result of these effects, the stem hip prosthesis cannot remain in the body for long period of time. Thus, this prosthesis is better for people over the age of 60.

In addition, in 1940, the procedure of a resurfacing hip replacement (RHR) was introduced, and recently its use has becoming popular, with both short- and medium-term reviews showing favorable results for young people or patients with femoral necks which are in good shape. However, long-term results are still awaited. The advantages of the RHR technique include the preservation of bone stock, a short rehabilitation period due to the less extensive surgery and the possibility of revision to a regular total hip prosthesis. However, some authors dispute these favorable results pointing out that the bone is not preserved and that both femoral head resorption and acetabular defects lead to subsequent early failure.

In general, there are few factors resulting in proximal femoral resorption by an implanted prosthesis: 1) stress shielding underneath the device, 2) progressive resorption due to an initial mismatch between bone and prosthesis leading to subsequent bone resorption and 3) compromised vascularity of the femoral head with subsequent osteonecrosis.

More specifically, previous studies have discovered that the major reasons for the vertical migration and subsidence of the femoral component in hip replacement, which causes the likelihood of loosening of the device, accurately, are:

1) From material properties point of view, cancellous bone is very different from cortical bone and metal. For example, the elastic modulus of the cortical bone, cancellous bone and stem prosthesis (CoCrMo) are $17.3 \times 10^9$, $324.6 \times 10^6$ and $196 \times 10^9$ (Pa), respectively. In principle, cancellous bone cannot support any load at all. Once cancellous bone comes in contact with the hard surface of metal stem and is loaded with a force beyond its physiological limits, plastic deformation occurs, which accumulates over an extended period of time and manifests itself as migration of the prosthesis.

2) There are changes and differences in the way force is loaded and distributed on the neck of the femur of an intact femur and an implanted stem prosthesis. According to Wolff's law, changes in stress distribution throughout the bone eventually causes definite alteration in its internal structure. For example, the strain applied on femoral head is radially transferred along the length of the stem. This causes a compression force from femoral head to be applied only on inner wall of shaft femur, concentrated on a small and local area of the medullas channel. This leads to local plastic deformation of the cancellous bone.

3) Current surgical procedures of stem THA generally requires the removal of the entire head and neck portion as well as some hard outer cortical bone in order to open the intramedullar canal and install the prosthesis. Such surgery imposes a lot of anatomical changes on the natural system, in terms of blood circulation and nutrient supply to affected area, that it also causes further physical changes in proximal femur with respect to bone quality after the surgery. These problems have been recognized by the orthopaedic community for quite some time. Obviously, these problems are associated with the current design of the hip prosthesis. Aseptic loosening, fatigue fracture, postoperative infection and stress shielding, can directly or indirectly relate to the stem-style design of the prosthesis with respect to weaknesses in both biomechanical and physiological outcomes from the existing THA.

The average 10-15 year survival rate of a total hip replacement (THR) in patients, particularly in patients younger than 55 years, is only 70% or less. The outcome of THA is dependent on its installation, the bone quality of patient and the activity of patient. However, the relatively poor survival rate suggests the need for an alternate method for replacing degenerative hips in this group of patients.

There have been several inventions of femoral prostheses issued previously which described non-stem construction of femoral prosthesis and intended retention the femoral neck. Most of them focus on either the replacement of the defective femoral head, which eliminates overcutting of healthy bone from patient or propose a stabilization of prosthesis on outside of proximal femur. For example, U.S. Pat. No. 5,133,769 (Wagner) teaches the cap for a femoral head, which can be imbedded without the use of cement. U.S. Pat. No. 4,976,740 (Kleiner) describes an anchored femoral dome that can be abutted with a sculpted femoral head through mechanical fastenings. U.S. Pat. No. 5,725,593 (Caracciolo) describes a total anatomic hip prosthesis which applied a cap on the defective femoral head with anchorage means fitting by pressure the acetabulum in the iliac fossa. These technologies all have their limitations and can not be widely applied. Due to the large variation of femoral head sizes between patients, it is difficult to develop a device which matches each individual one. In most cases, the femoral neck has more or less been damaged, so that it can not fully support the load from new head, even though the head has been repaired.

There have been ideas for a stemless femoral prosthesis in past. U.S. Pat. No. 6,488,716 (Huang) describes a prosthesis with a hollow cylinder shape and could be encased in outer area of a shaped femoral neck, in order to limit unnecessary cutting of femoral bone during THA. The prosthesis was fastened by one center screw through its body and expected a bio-mechanical fixation via the growth of new bone around it. There were a few successful cases in its clinical past, but it has explored defects in its design. Primarily, it was difficult to shape the retained portion of the femoral neck to match internal shape of the prosthesis, causing the existence of micro movements of the prosthesis around the neck, particularly in early stages of rehabilitation. In order to stabilize the prosthesis on the remnant neck, the fastening screw played a critical role. This caused too much stress to be applied on the screw and on the bone around the area the screw engaged. This resulted in either screw breakage or bone resorption. So it was hard to maintain the prosthesis in a stable condition. A same problem has happened in U.S. Pat. No. 7,458,990 (Chieng). The device claimed has also a significant shoulder section on its top. Furthermore, a taller cylinder section of the prosthesis was required to obtain an enough contact surface area of the prosthesis with femoral neck, which reduced the swing range of prosthesis motion. The angle of its motion was far less than 120 degree. The reduced range of motion (ROM) resulting from this total hip replacement (THR) leads to frequent prosthetic impingement, which may restrict activities of daily living and cause loss or dislocation of acetabular components. In practice, such a femoral prosthesis has a limited range of patient condition applications and difficulties in clinical use.

In 990 by Chieng and 716 by Huang also teach "wherein the main body further comprises at least one hole, the at least one hole adaptable for receiving a fastener configured to be fixed onto a femur". Here the major function of the fastener on the flange is to fix the prosthesis on the bone surface in order to further stabilizing the prosthesis thereon and reducing the strength on the center screw. But the problem is: the fastener works, like a regular nail or bolt, as a manner as that the nail tightly presses the object on a surface of bone by its small transversal section area of the nail head. Amount of holding force is proportional to friction of nail surface with bone imbedded and depends upon the quality of the base it sited on. A direction of the pressing force (it is same as well as resistance force against dragging the nail out) is along its axial direction. In other word, the nail penetrating into and being pulled out from bone are in same manner along same direction of track as well as a manner of installation of the device self. In this manner the nail could provide some effort resistance by its contact with bone surrounded, but not effort arm length of the main body, because the direction of that nail hammed into is same as the direction of that the nail peels away as well as a manner of prosthesis peels away. When load force on the load arm of the prosthesis takes in place and is beyond the loading ability of the center screw and bone around it, the device and the nail move together along same direction and peels away from the bone surface, like a manner of that a hammer drags the nail out. In soft bone area, like lateral tissue of the trochanteric bed, such a friction from nail won't provide much force for holding the prosthesis on site as one expected, because its bone quality is relatively soft.

Accordingly, there exists a need for an improved joint prosthesis, which addresses the needs and problems of prior joint designs as it relates to the distribution of stress and maintaining good bone condition.

From a practical point of view, in the case of a young patient, besides a diseased femoral head, most of the surface and the subsurface bone tissue around proximal femur are actually quite healthy, particularly the neck portion of femur. In these situations, it is undesirable to remove the healthy portion of the femoral neck. It has been recognized in previous studies that the femoral neck and the inferior medial ridge of the femoral shaft, particularly the medial neck cortex of femur, play a very important role in both loading and conducting compression force on proximal femur. Thus, the retention of the femoral neck and conducting the load through cortical bone of femur is a very important requirement for designing a new prosthesis hip and developing a new procedure for its implantation.

In addition, the stemless femoral prosthesis would eliminate most of problems caused by the stem type prosthesis, but it encounters some problems in its installation and maintaining stability in early stage. More specifically, the stemless prosthesis does not have the same advantage as stem prosthesis which sits in the peripheral cavity in proximal femur, providing more contact surface and stability in the early stage after installation. Therefore how to stabilize the stemless prosthesis on site is a key issue for its success.

SUMMARY OF INVENTION

In light of foregoing problems with prior art, particularly, of the existing femoral prosthesis and procedures, it is a goal of the present invention to provide a femoral component for THA, by which patient will no longer require the removal of the entire femoral neck and the prosthesis will not occupy intra-medullar bone of shaft anymore. Beyond that, the rigid stem(s) solidly extended from the lower rim of the component have largely lengthened the effort arm and increased the effort force of the component when it penetrated into inside bone of trochanteric bed. Particularly, it has created a second effort arm in lateral direction. It has largely expanded ability of the first, medial effort arm of the shall. Secondly, the stem has also coupled with the anchoring means for interlocking the component on remnant of proximal femur due to they are titled each other, when installed. Such a function is able to allow the prosthesis is fixed on the bone surface without tightly pressed. Both functions have significantly enhanced ability of the stability of the component on the site regardless the quality of the bone it sits on.

The object of present invention is to provide an ideal solution, in terms of the medial wall of the cup asymmetrically extended toward inferior medial ridge of the femur provides a longer effort arm length and wide distal opened envelop, which forms a large contact surface and volume of the cavity configured for housing on asymmetrically reamed proximal femur. By same token, more medial section of the wall prolongated toward inferior medial ridge area and more solid base the component sited on.

Another goal of the present invention is that a peripheral wall with an asymmetrical bell shaped inner contour provides an ideal manner to install femoral prosthesis into human body and eliminate the damage and changes on the anatomic structure of proximal femur, in terms of its biological structure and its blood flow, for example, typically to prevent overcutting bone stock on the medial side of the femoral neck. This would be an ideal solution for younger (20 years old or up) patients, who are more active and require a longer lifetime of the device. Obviously, there are no damages to the intra-medullar canal and bone marrow of proximal femur by such method. The new device would not obstruct any bone growth in both the medullar and shaft of femur of a young patient.

Still another goal of the present invention is provide fastening method (distal stem coupling with the anchoring means) for the femoral prosthesis, that is no longer a fasten manner by assistance from screw or nail. The interlocking system from the center screw and distal legs firmly anchors the prosthesis on the site with a proper tightness. It has expanded application for many more patients, regardless patient age, quality of bone or disease, which caused the hip defect. Furthermore, the present invention allows a patient to be substantially completely mobile after the operation and a shorter recovery period, because of 1) a simple operative technique, less damage of bone and a shorter period of the operation time and 2) a better interface between prosthesis and remnant femur due multiple mechanical fastenings and biological fastenings applied in the prosthesis. In addition, even if such an implanted femoral prosthesis were to fail at a later stage, it may be easily repaired, removed or replaced by another surgery, which could be a new same type of prosthesis or stem type one. It will expand the entire life span of artificial joint in human body. It will give more hope and promise for young patients.

BRIEF DESCRIPTION OF DRAWINGS

FIG. 3b. A detail description of an external proximal femoral prosthesis, in both posterior and medial views, respectively.

DETAILED DESCRIPTION OF PREFERRED EMBODIMENTS

Figures 1, 2:
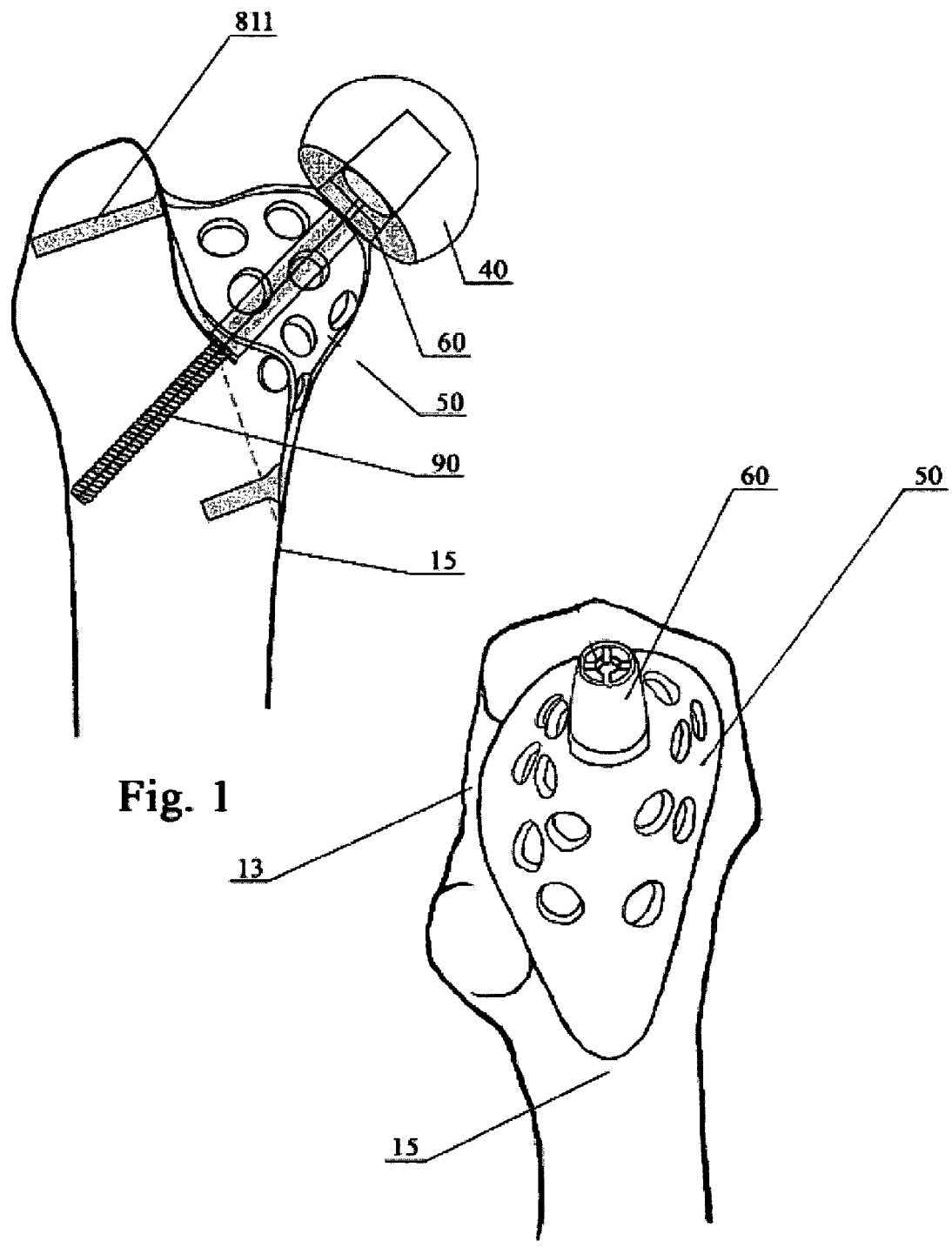
FIG. 1. A posterior view of an external proximal femoral prosthesis (left) attached on shaped proximal femur.
FIG. 2. A medial view an external proximal femoral prosthesis (left) attached on shaped proximal femur.
Figure 3A:
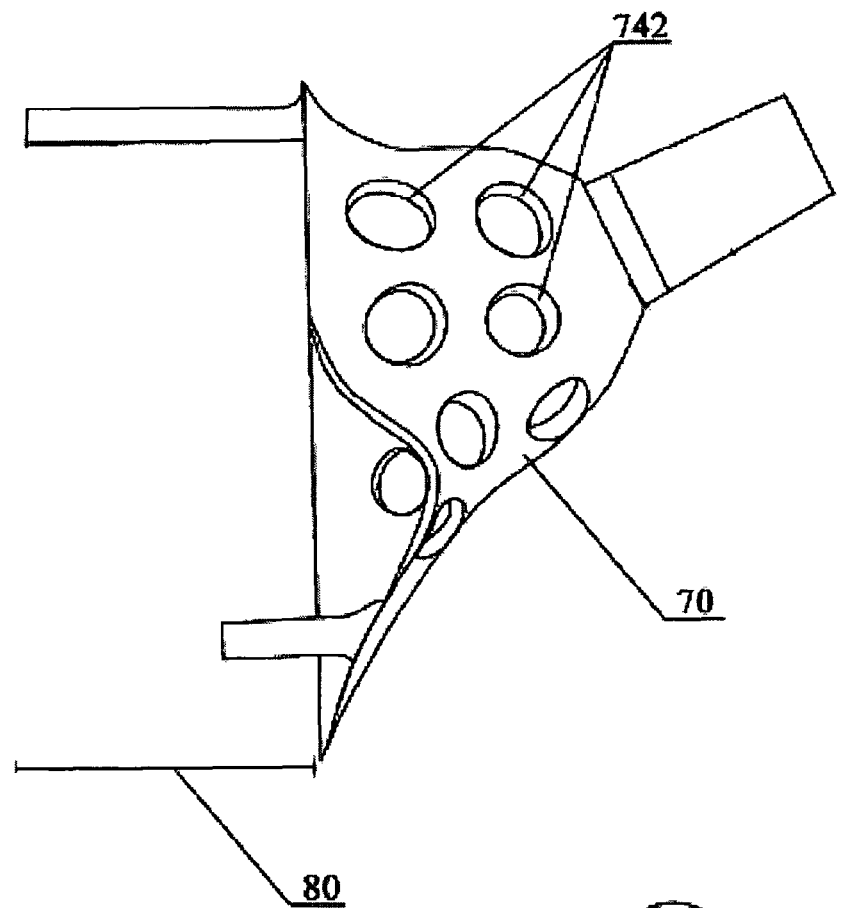
FIG. 3a. A posterior and medial view of an external proximal femoral prosthesis, respectively.
Figure 3A:
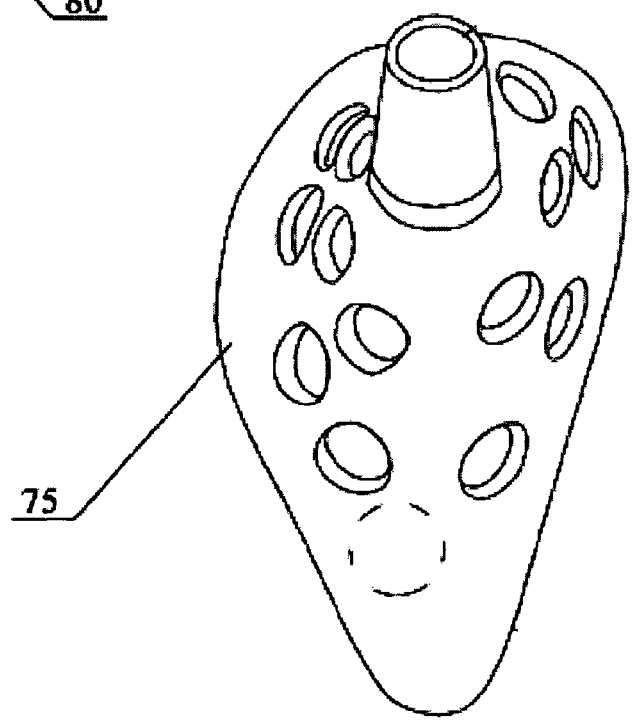

The present invention is directed to an external proximal femoral prosthesis for THA. Referring to FIGS. 1, and 2, in general, the shell (50) of prosthesis has defined as a hollow bell shape cup with an asymmetric wall configuration, more particularly, extended along direction of inferior medial ridge of the proximal femur for housing into outside retention of either the left or right proximal femur, respectively, by anchoring means for mechanically attaching and securing the shell to the external surface of proximal femur. More particularly, certain aspects of the present invention are directed to a femoral prosthesis that comprises several key features that provide an optimum configuration of the following factors:

(1) A minimum removal of bone during implantation, particularly retaining the femoral neck and keep the intramedullar canal of shaft in functioning, which could avoid any side-effect associated with opening intramedullar canal of the shaft.

(2) A broad contact area and stability of the implant on cortex bone surface, such as the inferior medial ridge area of femoral shaft, as well as maximum ease of installation of the prosthesis, instead only encased on the femoral neck, trochantic bed area and nearby described in the prior art.

(3) To maintain as most as possible loading stress fashion applied on cortex bone of the femoral inferior medial ridge and to keep remnant of bone in better shape, the stress from the head must be well distributed on the shell and is further conducted into the cortical bone through body of shell instead loading on cancellous bone of the femur through the stem. In addition, the medial wall section of the shell extended and covering inferior medial ridge would extend the effort arm length of the shell from the fulcrum of the component, which further enhances the loading ability of the prosthesis.

Referring to drawings, a preferred embodiment of left femoral component is illustrated in FIG. 1. It should be noted that, while the description of the invention and the related figures are directed the left femoral component, the present invention is also applicable to a right femoral component, which is merely a minor image of the left component described and illustrated herein.

As detailed of a preferred embodiment said shell 50 has a longitudinal axis 51. It is defined an axis which configured to be substantially coaxial with a longitudinal axis 16 of natural femoral neck 12. So in other word, said longitudinal axis 51 of said shell would form a inclination angle 52 with the femoral shaft (long bone) from a range of about 115 to about 145 degrees and anteversion angle with the plane of the human body from about 6 to about 16 degrees, if said shell is implanted on the site. Because of coaxial of the longitudinal axis 51 and 16, when said shell is implanted, a new inclination angle 52 and anteversion angle from the prosthesis would be same or very close to anatomical angles of femoral shaft from a particular patient.

As described in FIGS. 1, 2, 3a and 3b, said shell 50 comprises following portions: a neck object portion 60 for pairing with cavity of the articulation head element by self-holding taper configuration. a substantially hollow cup having asymmetrical thin and peripheral wall portion 70 outwardly extended from a lower end of the object 60 and having wide opened lower rim. It dimensioned to encase the outer surface of the proximal femur; which has also been reamed with asymmetrical bell shaped outline and elongated distal stem portion 80, as gaplessly continues piece of the shell, downwardly extended from the lower rim of the peripheral wall.

Said peripheral wall 70 possesses an inner contour configured to envelop exterior surfaces of the remnant neck (lower portion at ½ level or lower) and trochanteric bed as well as inferior medial ridge of proximal shaft 12, respectively. Its dimension of the inner contour has a plurality of transverse cross sections along a view of said longitudinal axis, so configured with a smaller cross section area on the upper rim (less shoulder area) and a large cross section area on the lower rim (broad contact area below the neck section), which is closely matching the exterior transverse cross contour of a lower and sculpted femoral neck 12 and therebelow. Since the inferior medial ridge of the femoral shaft has a bone distribution with most condensed density and withstands as well conducts most loading force in the nature proximal femur, less trimming bone in this area would keep the neck and proximal femur in full function. If do so, the remnant surface of the reamed femoral neck would likely be reamed as asymmetrical bell shaped outline. Said wall 70 has been hollowed by a plurality of apertures 742. The shape of said apertures has configured open windows selected from the group consisting of: a plurality of round hole, elongated round hole and others thereof. Said apertures 742 on said wall 70 are well distributed on area around posterior and anterior face of said wall 70 and but not in a middle section (lateral and medial side) between them, which is considered as a major area where loading stress is distributed. Said apertures 742 on said wall 70 serve a function of bio-fixing the component on site by new bone growing therethrough.

According to the mechanics of the leverage: Load arm multiplies load force=effort arm multiplies effort force: $L_{load} \times F_{load} = L_{effort} \times F_{effort}$. Any increment from either effort arm $L_{effort}$, and effort force, $F_{effort}$, would gain ability (the moment) of component against increment from opposite side of the equation. Asymmetrical extension of the medial wall section along femoral crest provides more effort arm length, $L_{effort}$, of the shell with a respect the fulcrum point of the shell, which locates on the cross point of the bottom plane of the peripheral wall and the longitude axis. Said peripheral wall of said cup 70, in principle, is radially, outwardly, uninterrupted flaring from the upper rim of the wall to the lower end thereof to form a cavity having narrow cross section on top and wide distal opened end, particularly in lateral, and posterior and medial direction, respectively. More particularly, in said medial direction, said medial section of the wall is continually elongating along the inferior medial ridge of the femoral shaft toward covering the inferior ridge region of femur and forms "tongue-like" shape collar. Said medial wall along the medial direction of said cup covers area or region along the inferior medial ridge of the femur, which has an elongated "tongue-like" shape and more flat (less sloped) than other section of lower rim The medial wall section 754 shown asymmetrical bell shape will embed upon the outer surface of the inferior medial ridge, which is considered as an area with higher thickness and hardness in femoral bone and is able to load more compressive stress. In fact, this area is also to have more chance for new bone generation, if there is proper stress or stimulation acted on. So said peripheral wall 70 of said hollow cup possesses a proper shape, which closely follows the shaped proximal femur. Such a structure would offer the component advantages: 1) The larger cavity formed, particular by the asymmetrical bell shape medial wall section, closely mates the inferior medial ridge of the shaped proximal femur, which has less cutting and keeps most of bone stock in position and ideal bone thickness, and possesses a broader contact region therebetween. 2) The lower altitude along the longitudinal axis/no shoulder on upper portion of the component has significantly reduced the chance of impingement. 3) Asymmetric profile of the cavity formed also to prevent rotations of the component around the longitude axis. 4) Because large volume of the cavity formed, less bone reamed from femur could be expected in most case, particularly, more bone-conserving in inferior medial ridge of the femur. More bone stock remained, more chance for both patient and surgeon in revision case in the future. 5) As much as the medial wall extended along inferior medial ridge of the proximal femoral shaft, longer effort arm length of the component possessed. It would contribute a lot on stabilizing the component against heavy load.

According to loading pattern of the prosthesis, the medial wall of the prosthesis conducts most of loading stress from ball head down to the bone surface, when strength acted on it. Rest of wall section has no such a function at all. Since the stem(s), as gaplessly continues piece of the shell, has downwardly extended from the lower rim of the peripheral wall 70 and will penetrated into bone of proximal femur, the effort arm length $L_{effort}$, of the shell has be further increased with a respect of the its length of the load arm, which is equal to a distance between the center point of the ball and the fulcrum of the shell sited on the femur. By such arrangement, the stem would moves with the shell together, when the shell under stress. So the surface area of the stem(s) exposed to bone embedded would increase the effort force (resistance) of the shell as well, because it will move or affort on bone surface along its radial direction. As far as the stem penetrated into the inside of the bone, the more resistance and more arm length, $L_{effort}$, the shell possessed. In comparison, the resistance of the stem, $F_{effort}$, comes from the radial direction of the stem instead one from the cross section along its axial direction of the fastening nail. The virtual acting area of the stem(s) is proportion to the length of the stem and equal one half of contact area between stem and bone. In addition, since there is a distal stem extended on lower rim of lateral wall, the lateral wall becomes a burden wall and is able to share the stress from the ball head, which is double the loading ability of the shell and distracts stress on the bone surface. Said distal stem portion 80 serves a function of further lengthening the effort arm, $L_{effort}$, and increasing the effort force (resistance), $F_{effort}$, of the shell in order to stabilize said shell on femoral remnant of the bone. The distal stem portion 80 possesses at least one elongated stem 811, by way of example and not by way limitation, which is solidly extended from and is integral with lower rim of said wall 70 of said cup 50. The preferred number of stems is two. Thereby, the first stem 811A of said distal stem portion preferred located at area between the lesser trochanter and inferior medial ridge of femoral shaft. The second one 811B preferred located at area between a lateral root of femoral neck and greater trochanter.

Figure 4:
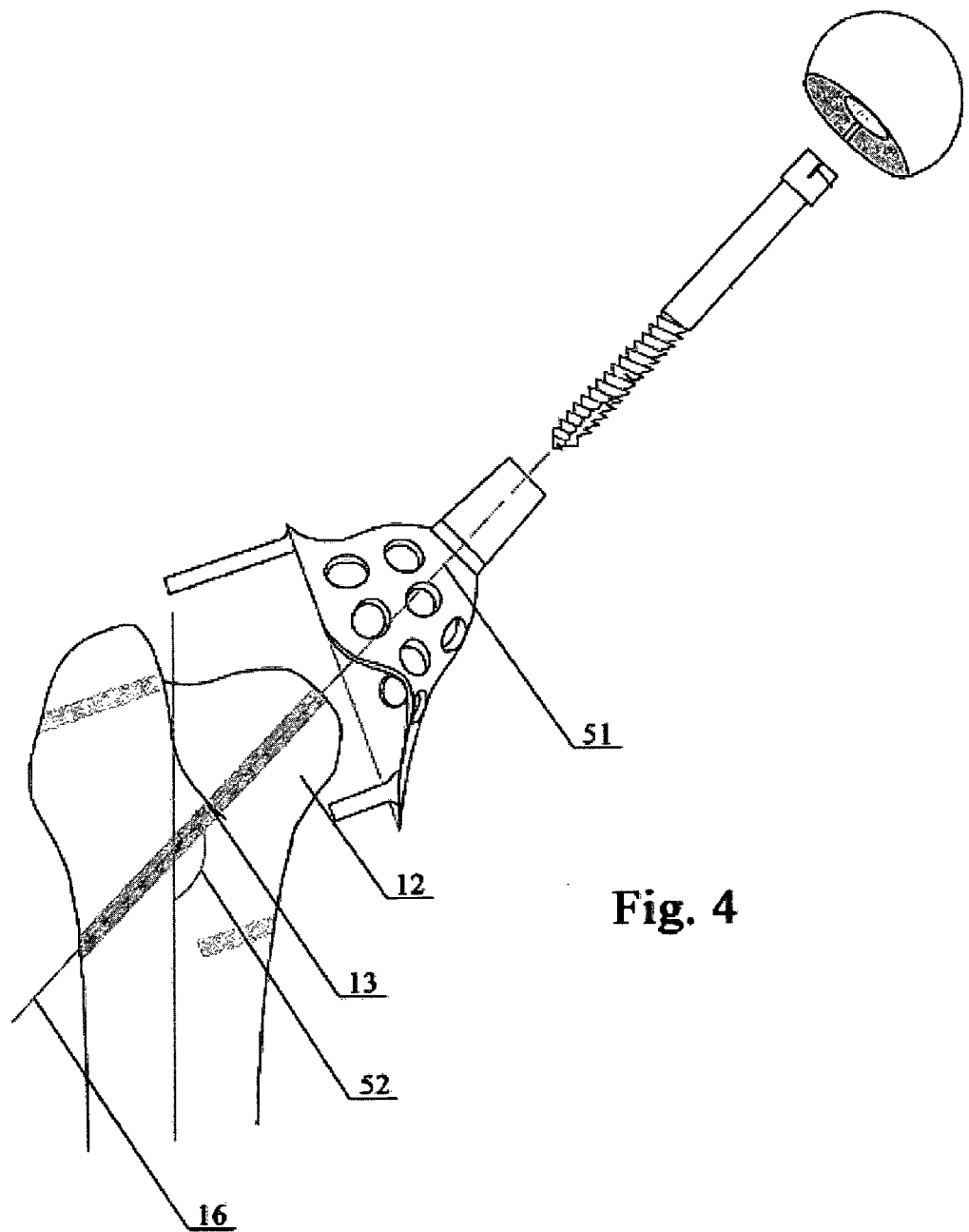
FIG. 4. A schematic drawing: a typical sample of assembling prosthetic parts along the inclination angle of femoral shaft.
Figure 5:
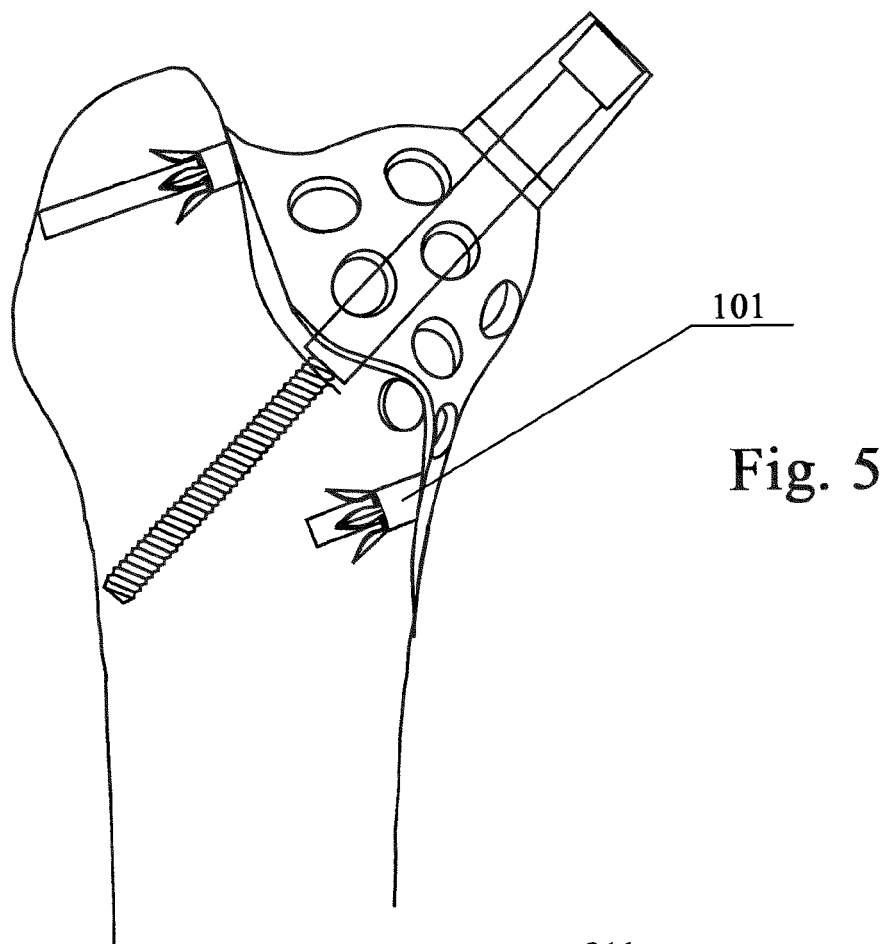
Figure 6:
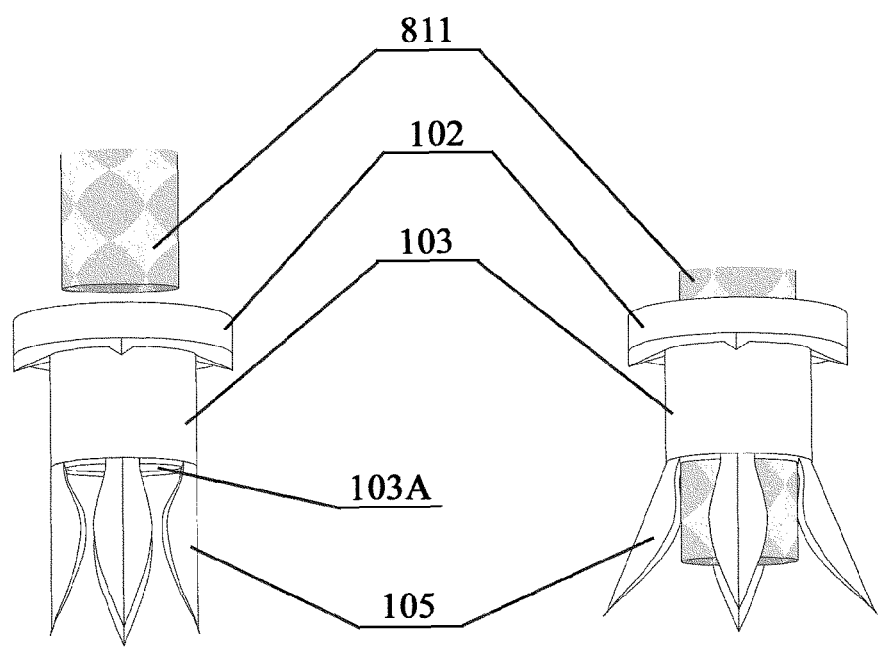
Figure 7:
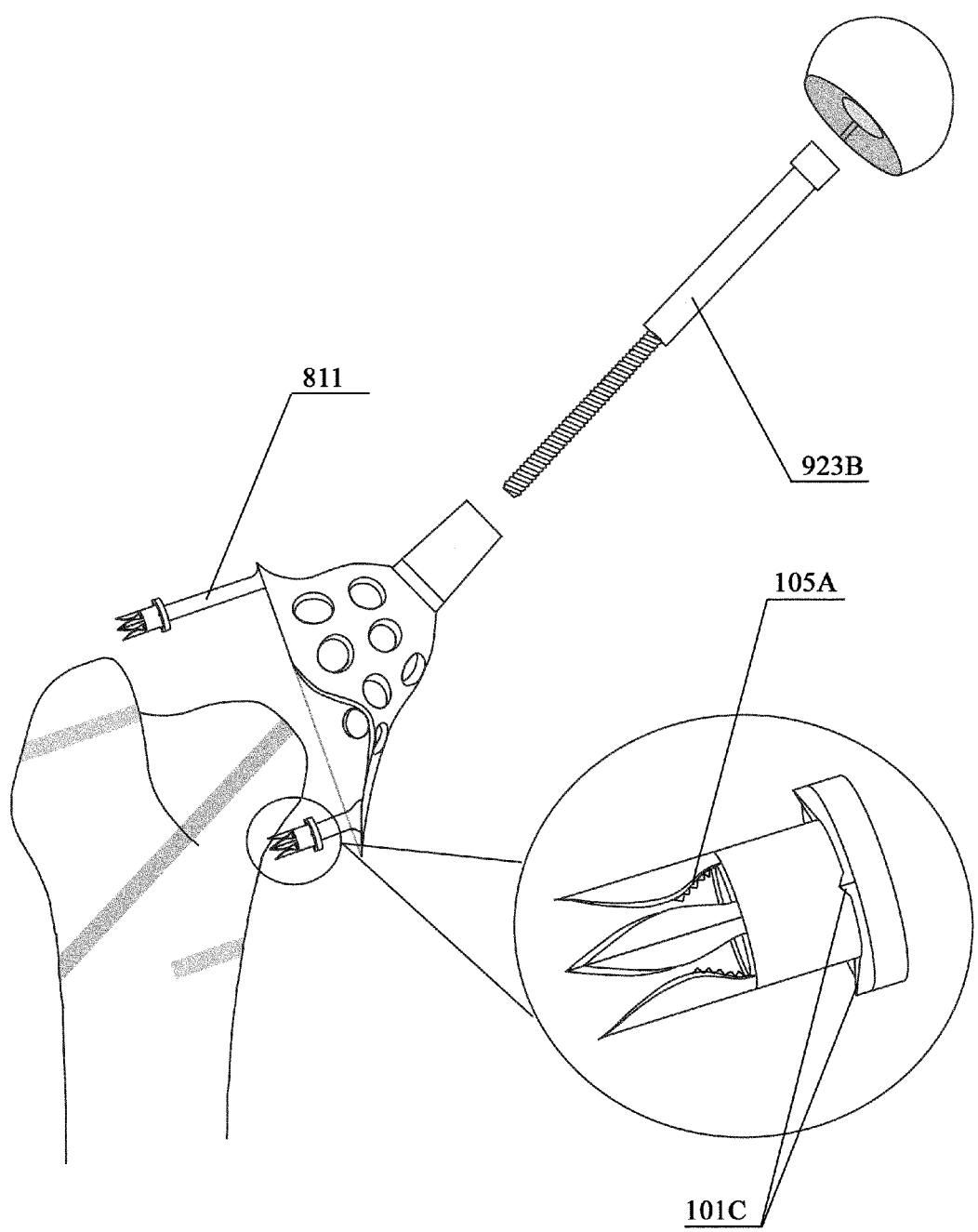
Figure 8:
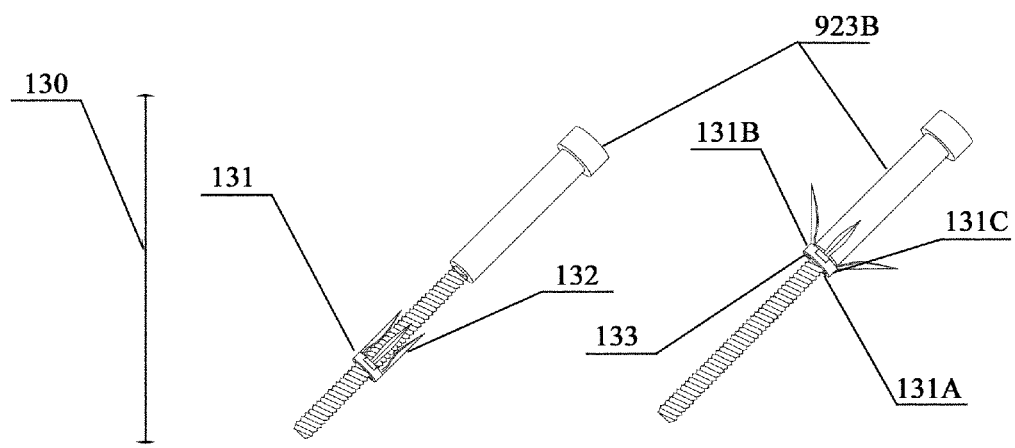
Figure 8:
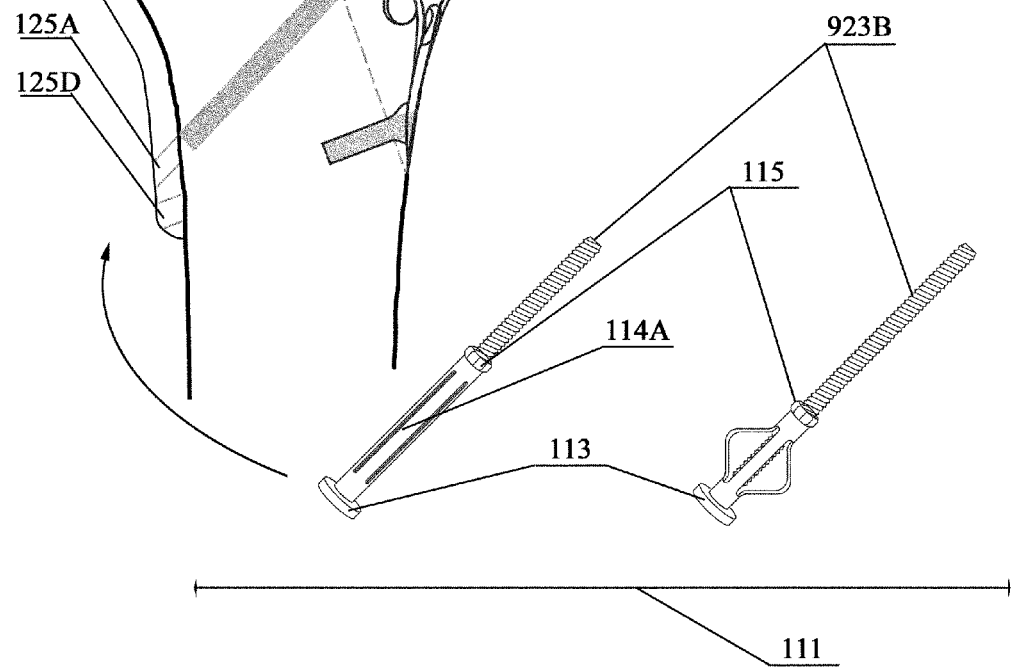

A longitudinal axis of the stem 811 is perpendicularly to a bottom plane 741 of said cupu 70 and have tilted certain angle from the longitudinal axis of the component (in FIG. 4). A length of said stems is selected from the group consisting of, when said component installed, i. stem 811 is long enough for being inserted (through area near to, but not on, greater trochanter and lesser trochanter) and staying with intra-medullar tissue of femur, and ii. stem 811 is long enough to be laterally extended through lateral cortical bone of the femur and inserted (joined with) into a lateral plate.

In more detail, the stem(s) 811 serve functions of: 1. Largely extending the effort arm and effort force of the prosthesis toward its fulcrum in order to further withstand plummet force from the femoral head, when it stays in intra-medullar tissue of femur. 2. coupling with the tension anchoring means to firmly fasten the prosthesis on remnant of the proximal femur, when the prosthesis is implanted; and 3. Penetration of stem(s) through cortical bone and remaining into intra-medullar bone further increases contact area between the prosthesis and the remnant of femur. In other word, when the loading force acts on the ball, unlike pulling out the nail from the site, the moving track of the stem is to make a turn around the fulcrum of the prosthesis inside the bone. So the longer effort arm length of the stem(s) and enough contact area between stem and bone sited would provide much more resistance of withstanding the plummet turning from the ball. In that design, the concerns on the bone quality around stem becomes less important, because stem has wide contact area with the bone. In short, when loading force acts on the ball, the direction of the corresponding motion of the stem(s) and the component are quite different. To obey same principle discussed above, formation of screw-stem locking system by cooperating elongated stem(s) with tension anchor means, such a center screw, is able to interlock the prosthesis onto remnant of natural proximal femur, which significantly reduces a burden of the center screw and chance of micro motion of the prosthesis under maximum loading impact. In a preferred embodiment, the length of the stem is about 5 to 30 mm long and number of stem is 2 to 3. There can be texture 812 on outside surface of said stem 811. In addition, since most of the lateral cortical bone is more soft than one of the inferior medial ridge, it is hard to expect such bone is able to stand concentrated stress, no matter it is from the screw or nail. Any fastening means applied on this area would be easely dragged out, like a hammer drags nail out from wood or wall. So the stem here plays a role of that it extends the contact area between bone and prosthesis and change acting direction against the stress.

There can be texture on outside surface of the said stem 811. Such a texture 812 could be saw-tooth like ribs, spike, or protrusions on outside surfaces of the stem.

Said distal stem portion 80 could also be assembled as a pin or screws at least on one screw-threaded hole (not shown) of the cup, by way of example and not by way limitation, on the lower rim of said cup 70 (of, but not on, greater trochanter and lesser trochanter). More preferred arrangement of said threaded holes would be at least two of them in separated location. The first one is preferred located at area near the lateral root of femoral neck. The second one preferred located at area between the lesser trochanter and inferior medial ridge of femoral shaft. Accordance of this configuration, a function of the thread hole(s) serves a base for the thread pin(s). So said elongated pin with thread at its proximal end, in a preferred embodiment, could couple with an anchoring rivet to penetrate into either intra-medullar tissue of femur and screw through the hole. In another preferred embodiment, the end section of said threaded pin could further passes through the lateral cortices and joint with or inserted into the bore on said lateral plate.

In additional preferred embodiment of the distal stem portion, a function of the threaded hole(s) and serve for accepting said threaded fastening screw from lateral side of femur, which passes through bores on said lateral plate, intra-medullar tissue and engages on such holes. Such a connection between said shell and said lateral plate would increase a stability of shell implanted against large amount of stress and provide a broader application of the component, particularly in concerns of differing bone quality of femur of various patients.

The anchoring means here is selected from selection of either a self-tapping screw or a thread bolt. In one preferred embodiment, when the anchoring means fastens the component on the site, the self-tapping screw passes through the center hole of the object 60 first and then screws into the cortex bone on lateral side of the femur. In another embodiment, the thread bolt passes through the center hole of the object 60, then joints with the lateral plate on the lateral side of the femur, if the bone quality of the patient is not good enough or has less density.

The specific dimensions of feature of any devices in the present invention can be readily varied depending upon the intended application, as will be apparent to those of skill in the art in view of the disclosure herein.

The foregoing disclosure and description of the invention are illustrative and explanatory thereof, and various changes in the size, shape, materials, arrangement and procedure, as well as in the details of the illustrated construction may be made without departing from the spirit of the invention. It is to be understood that the invention is not limited to the particular embodiments described above, but is solely limited by the scope of the appended claims.

What is claimed is:

1. An external femoral prosthetic component for housing the outside of a remnant of natural proximal femur and coupling with articulation components for use in total hip arthroplasty comprising:
   A) a hollow shell having a distal opening adapted to attach to a natural proximal femoral neck of a patient and an oppositely extending proximal end, said hollow shell further comprising a neck portion attached to the proximal end of said hollow shell, said hollow shell being an asymmetrical bell-shaped cup with a distal wide opened cavity, said hollow shell further comprising at least one elongated leg rigidly attached to a distal portion of said hollow shell, said elongated leg and said hollow shell together being a one-piece monolithic component, wherein said hollow shell and elongated leg function to increase effort moment of said shell when implanted into said patient by distributing patient loading force on the shell into a shaft of the proximal femur; and
   B) a plurality of tension anchoring means adapted to mechanically fasten said shell onto said remnant of proximal femur by interlocking mechanisms.

2. The femoral component of the claim 1, wherein said shell has a longitudinal axis which is coaxial with the longitudinal axis of a neck of the proximal femur and wherein said neck portion upwardly protrudes from an upper rim of said bell-shaped cup along the longitudinal axis of said shell, said neck portion having a center through-hole for coupling with the tension anchoring means, said neck portion being configured with an exterior self-holding taper for pairing with a cavity of an articulation element.

3. The femoral component of the claim 2, wherein said bell-shaped cup comprises a shoulder, a circumferential wall and a peripheral collar, and having at least one aperture thereon and is downwardly flared out from a lower end of said neck portion along a direction of a medial ridge of the proximal femoral shaft in order to mantle the profile of the natural proximal femur including an external surface around an inferior neck, trochanterical bed and inferior medial ridge of the proximal femoral shaft, said inferior medial ridge of said proximal femoral shaft mantled by a medial wall of said bell-shaped cup.

4. The femoral component of the claim 3, wherein said elongated leg has a longitudinal axis which is perpendicular to a bottom plane of the circumferential wall, said longitudinal axis of said elongated leg being tilted from the longitudinal axis of the shell, said elongated leg configured to penetrate through cortical bone and secure to intramedullar bone and couple with said tension anchoring means.

5. The femoral component of claim 1, said hollow shell comprising two elongated legs rigidly attached to a distal portion of said hollow shell.

6. The femoral component of claim 5, wherein a first elongated leg is positioned on said bell-shaped cup such that it is adapted to extend into an area near a lateral root of said proximal femoral shaft, and a second elongated leg is positioned on said bell-shaped cup such that it is adapted to extend into an area between a posterior root and a lesser trochanter of said proximal femoral shaft.

7. The femoral component of claim 1, wherein said bell-shaped cup comprises a shoulder, a circumferential wall and a peripheral collar, and is downwardly flared out from a lower end of said neck portion along a direction of a medial ridge of the proximal femoral shaft in order to mantle the profile of the natural proximal femur including an external surface around an inferior neck, trochanterical bed and inferior medial ridge of the proximal femoral shaft, said inferior medial ridge of said proximal femoral shaft mantled by a medial wall of said bell-shaped cup.

8. The femoral component of claim 7, further wherein said collar in a lateral direction is shaped such that it is adapted to mantle a femoral area between a lateral root of the proximal femoral neck toward the greater trochanter, said collar in a posterior direction is shaped such that it is adapted to mantle a femoral area between a posterior root of the proximal femoral neck and a trochantic crest, and said collar in a medial direction is shaped such that it is adapted to mantle a medial root of the proximal femoral neck and the inferior medial ridge of said proximal femoral shaft.

* * * * *